US009188565B2

(12) United States Patent
Glish et al.

(10) Patent No.: US 9,188,565 B2
(45) Date of Patent: Nov. 17, 2015

(54) HIGH FIELD ASYMMETRIC ION MOBILITY SPECTROMETRY (FAIMS) METHODS AND DEVICES WITH VOLTAGE-GAS COMPOSITION LINKED SCANS

(75) Inventors: Gary Glish, Chapel Hill, NC (US); Mark Ridgeway, Billerica, MA (US); Alice Pilo, West Lafayette, IN (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/485,346

(22) Filed: May 31, 2012

(65) Prior Publication Data

US 2013/0320205 A1    Dec. 5, 2013

(51) Int. Cl.
*H01J 49/00* (2006.01)
*G01N 27/62* (2006.01)

(52) U.S. Cl.
CPC .................................. *G01N 27/624* (2013.01)

(58) Field of Classification Search
CPC ......... H01J 49/00; H01J 49/02; H01J 49/005; H01J 49/008
USPC ......... 250/281, 282, 283, 286, 288, 290, 291, 250/292, 293, 294
See application file for complete search history.

(56) References Cited

U.S. PATENT DOCUMENTS

| | | | |
|---|---|---|---|
| 4,849,628 A | 7/1989 | McLuckey et al. | |
| 5,206,509 A | 4/1993 | McLuckey et al. | |
| 5,420,424 A | 5/1995 | Carnahan | |
| 6,504,149 B2 | 1/2003 | Guevremont et al. | |
| 6,703,611 B2 | 3/2004 | Glish et al. | |
| 6,972,407 B2 | 12/2005 | Miller et al. | |
| 7,227,133 B2 | 6/2007 | Glish et al. | |
| 7,514,674 B2 | 4/2009 | Glish et al. | |
| 2003/0057369 A1* | 3/2003 | Guevremont et al. | 250/286 |
| 2003/0150985 A1* | 8/2003 | Guevremont et al. | 250/287 |
| 2005/0029445 A1* | 2/2005 | Lee et al. | 250/288 |
| 2005/0029449 A1* | 2/2005 | Miller et al. | 250/293 |
| 2005/0116160 A1* | 6/2005 | Guevremont | 250/282 |
| 2005/0161596 A1* | 7/2005 | Guevremont et al. | 250/294 |
| 2006/0027746 A1* | 2/2006 | Guevremont et al. | 250/292 |
| 2009/0057546 A1* | 3/2009 | Giles | 250/282 |
| 2009/0108195 A1* | 4/2009 | Guevremont et al. | 250/282 |
| 2009/0212207 A1* | 8/2009 | Griffin et al. | 250/282 |
| 2010/0171033 A1* | 7/2010 | Jolliffe et al. | 250/282 |
| 2010/0243883 A1* | 9/2010 | Vidal-De-Miguel | 250/282 |
| 2010/0282966 A1* | 11/2010 | Schneider et al. | 250/282 |

(Continued)

OTHER PUBLICATIONS

Steve O., RElationship between Temperature, Volume, and Pressure?, Jun. 3, 2008, Yahoo! Answers, <http://answers.yahoo.com/question/index?qid=20080603152042AAOMP7f>.*

(Continued)

*Primary Examiner* — Michael Logie
*Assistant Examiner* — Jason McCormack
(74) *Attorney, Agent, or Firm* — Jenkins, Wilson, Taylor & Hunt, P.A.

(57) ABSTRACT

Improved methods and devices for analysis of gas phase ions via ion mobility type analyzers, particularly high field asymmetric waveform ion mobility analyzers (FAIMS), by linking gas composition and/or flow rate with the scanning of compensation voltage or asymmetric waveform amplitude are provided. Linking these parameters results in improvements in resolution, sensitivity, and selectivity. The methods and devices according to the presently disclosed subject matter provide for the improvement in resolution for specific ions without affecting the entire FAIMS spectrum.

27 Claims, 15 Drawing Sheets

(56) References Cited

U.S. PATENT DOCUMENTS

| | | | |
|---|---|---|---|
| 2011/0036973 A1* | 2/2011 | Alonso et al. | 250/282 |
| 2011/0133076 A1* | 6/2011 | Miller et al. | 250/287 |
| 2012/0068061 A1* | 3/2012 | Griffin et al. | 250/282 |

OTHER PUBLICATIONS

Barnett et al., Separation of o-, m- and p-phthalic acids by high-field asymmetric waveform ion mobility spectrometry (FAIMS) using mixed carrier gases, Mass Spectrom. 35, 976-980(2000) John Wiley & Sons, Ltd.

Barnett et al., Evaluation of Carrier Gases for Use in High-Field Asymmetric Waveform Ion Mobility Spectrometry, J. Am. Soc. Mass Spectrom. 11:1125-1133 (2000) Published by Elsevier Science Inc.

Buryakov et al., A new method of separation of multi-atomic ions by mobility at atmospheric pressure using ahigh-frequency amplitude-asymmetric strong electric field, International Journal of Mass Spectrometry and Ion Processes 128. 143-148, (1993), Elsevier Science Publishers B.V., Arifov Institute of Electronics, Uzbek Academy of Sciences, Akademgorodok, 700143 Tashkent, Uzbekistan.

Ridgeway et al., Proceedings of the 58th ASMS Conference on Mass Spectrometry and Allied Topics, Salt Lake City, Utah, May 23-27, 2010.

Shvartsburg, et al., High-Resolution Differential Ion Mobility Separations Using Helium-Rich Gases, Anal Chem. Mar. 15, 2010; 82(6): 2456-2462. doi:10.1021/ac902852a. Biological Sciences Division, Pacific Northwest National Laboratory, P.O. Box 999, Richland, Washington 99352.

Shvartsburg, et al., Separation of Peptide Isomers with Variant Modified Sites by High-Resolution Differential Ion Mobility Spectrometry, Anal Chem. Oct. 1, 2010; 82(19): 8327-8334. doi:10.1021/ac101878a.

Xuan et al, High-field asymmetric waveform ion mobility spectrometry (FAIMS) coupled with high-resolution electron transfer dissociation mass spectrometry for the analysis of isobaric phosphopeptides, Rapid Commun Mass Spectrom, 2009; 23: 1963-1969, Thermo Fisher Scientific, 355 River Oaks Parkway, San Jose, CA 95134, USA, published online in Wiley InterScience (www.interscience.wiley.com) DOI: 10.1002/rcm.4101.

* cited by examiner

A.

| m/z | RP FOR NON-LINKED SCAN | RP FOR LINKED SCAN |
|---|---|---|
| 622 | 8.72 | 16.9 |
| 922 | 9.07 | 19.6 |
| 1522 | 5.64 | 38.9 | though the illustrated embodi-

HIGH FIELD ASYMMETRIC ION MOBILITY SPECTROMETRY (FAIMS) METHODS AND DEVICES WITH VOLTAGE-GAS COMPOSITION LINKED SCANS

TECHNICAL FIELD

The presently disclosed subject matter relates to the field of high field asymmetric waveform ion mobility spectrometry (FAIMS), and more particularly to methods and devices for the coordinated control of carrier gas composition and the voltages applied to a FAIMS analyzer.

BACKGROUND

The presently disclosed subject matter generally relates to improved methods and devices for the analysis of gas phase ions via ion mobility type analyzers, particularly high field asymmetric waveform ion mobility analyzers (FAIMS). FAIMS is a gas phase ion separation technique which utilizes the non-linear change in ion mobility as a function of electric field strength to filter ions (McDaniel and Mason, 1973).

There exists a need to improve the performance of FAIMS. Efforts to improve FAIMS performance, including, for instance: the use of planar geometry FAIMS devices instead of cylindrical devices; increasing the amplitude of the "high" portion of the electric field by improving power supply designs; decreasing the inter electrode distances thereby allowing an increase in the electric field without discharge; using chemical modifiers or carrier gas dopants; and modifying the composition of the carrier gas, have been met with limited success. However, each of the previously attempted methods of improving performance has come with an associated cost. For example, any improvement made to FAIMS performance in the prior art for one compound or class of compounds, by using a modified carrier gas for example, has come with a loss of performance for some other class of compounds. This loss in performance may reduce resolution, reduce peak capacity, or result in a loss of signal intensity. In addition, gas mixtures which contain a gas with a lower dielectric breakdown threshold, or include reactive gases may shorten the operational lifetime of the instrument.

Thus, the need to optimize FAIMS performance, including modifying the carrier gas composition in a compound specific manner in order to improve overall performance, still exists. The presently disclosed and claimed subject matter addresses this and other needs in the art.

SUMMARY

It is an object of the presently disclosed subject matter to provide methods and devices for voltage-gas composition linked scans in High Field Asymmetric Ion Mobility Spectrometry (FAIMS).

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 12A, 12B and 12C show the separation of both charge states of Angiotensin I (m/z 433 and m/z 649) at He concentrations of 0 L/min, 0.5 L/min and 1 L/min, respectively. The testing was conducted at DV=1.2 kV.

FIG. 13A presents the resulting data in tabular format. FIG. 13B is a graphical representation of the results from linked-scanning.

FIGS. 14A and 14B compare the resolution of ions with mass-to-charge values of 622, 922 and 1522, for non-linked scanning (FIG. 14A) and linked scanning (FIG. 14B). The data, including percent increasing in RP, is set out in tabular format in FIG. 14C.

FIG. 16A illustrates the waveform when He concentration is 0%. FIG. 16B illustrates the waveform when He concentration is 60%. Without being bound by any particular theory of operation, the results are believed to illustrate that introduction of He to the system causes the waveform to change (capacitance of system changes). No changes were made to settings of the power supplies.

DETAILED DESCRIPTION

Figure 1:
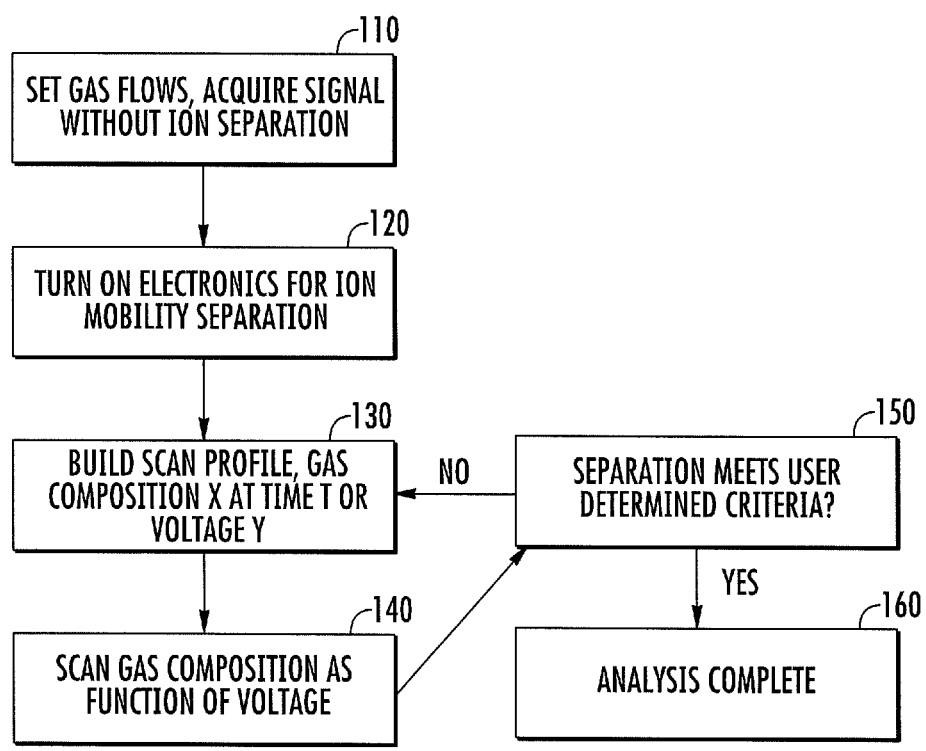
FIG. 1 shows a block flow diagram for the optimization of carrier gas composition as a function of FAIMS analyzer voltage or scan time.

High field asymmetric ion mobility spectrometry (FAIMS) separates gas phase ions based on the ratio of their mobilities in high and low electric fields. The presently disclosed subject matter generally relates to improved methods and devices for the analysis of gas phase ions via FAIMS. FAIMS is a gas phase ion separation technique which utilizes the non-linear change in ion mobility as a function of electric field strength (Buryakov et al., *J. Mass Spectrom. Ion Phys.* 128. 143, 1993) to filter ions. Above an electric field to gas density ratio (E/N) of approximately 40 Td (E>10,700 V/cm at atmospheric pressure) the mobility coefficient K(E) has a non-linear dependence on the field. K(E) also has a dependence on the gas in which the separation is performed. By varying the composition of the gas in which the separation is carried out the resolution and sensitivity of separation can be increased (Shvartsburg et al., 2010). This dependence is believed to be specific for each ion species. FAIMS is described in detail in the literature (Buryakov et al., 1993; Riegner et al., 1997; Carnahan et al., 1996; and U.S. Pat. No. 5,420,424). FAIMS devices disperse ions based on the difference in the mobility of an ion at high field ($K_H$) relative to its mobility at low field ($K_L$). That is, the ions are separated on the basis of the compound dependent behavior of mobility as a function of electric field strength in a gas or mixture of gases which typically does not change through the experiment. In FAIMS devices such as described in U.S. Pat. No. 6,972,407, herein incorporated by reference in its entirety, two parallel, planar conducting electrodes are used to generate an electric field in which analyte ions are to be analyzed. The analyte ions are entrained in a carrier gas which moves at high velocity (several meters per second) perpendicular to the electric field, i.e. parallel to the surface of the planar conducting electrodes. Applying the appropriate potentials to the "top" and "bottom" electrodes will result in the filtering of ions on the basis of the ratio of the ion mobility in "high" and "low" electric fields.

A rectangular (or approximately rectangular) waveform having repeatedly a high potential and then a low potential is applied between the electrodes. For a relatively short period of time, a high potential is applied between the electrodes and then for a longer period of time a relatively low potential of opposite polarity is applied. The magnitude of the potentials and the duration of their application are such that the time averaged potential difference is zero. During the application of the high potential, ions will move toward the electrode with the opposite polarity from the ion with a mobility $K_H$. During the application of the low potential of opposing polarity, the ions will move with a mobility $K_L$ and in the opposite direction to that when the high potential was applied. Applying an additional DC "compensation voltage" (CV) between the electrodes allows the selection of ions of a given mobility difference to be transmitted. The larger the difference in $K_H$ and $K_L$ of an ion the greater the CV required to transmit that selected ion.

FAIMS spectrometers may be operated as standalone ion filtering devices, but have seen more widespread use when combined with mass spectrometry. (See, e.g., U.S. Pat. No. 6,504,149.) This type of combined analyzer provides advantages over a mass spectrometer alone. For example, a combined FAIMS mass spectrometer has an improved signal-to-noise ratio over a mass spectrometer alone because the FAIMS device can filter away the chemical background. This feature becomes especially advantageous when combined with ion trapping mass analyzers, where the removal of chemical background allows an increase in the accumulation of ions of interest, effectively increasing signal abundance for a given ion. Further, FAIMS provides a way of separating ions of identical mass but differing structure such as the case of biological conformations, or chemical isomers thus creating an additional dimension of shape-to-charge ratio to FAIMS-mass analyzer instruments (Xuan et al., 2009; Shvartsburg et al., 2010).

In order to increase selectivity, resolution, and peak capacity in a FAIMS analyzer, and thereby optimize performance, a number of methodologies have been employed. For example, the use of planar geometry FAIMS devices versus cylindrical devices can result in higher resolution, but can be accompanied by lower ion transmission. Further improvements have been attempted by increasing the amplitude of the "high" portion of the electric field by improving power supply designs thus increasing the ratio of $K_H/K_L$ in some cases.

However, this approach is limited as the voltage applied to the FAIMS electrode will eventually reach the dielectric breakdown strength of the carrier gas causing a discharge to occur. Alternatively, some have decreased the inter electrode distances thereby allowing an increase in the electric field without discharge. However, this approach is also limited in that eventually the gaps become so small as to be impractical in terms of ion transmission and physical construction.

Optimizing the performance of FAIMS has also been attempted by adjusting temperature, pressure, and/or gas composition to affect $K_H$ and $K_L$ for a given ion. For example, the use of helium, a relatively low molecular mass gas, has been employed in an effort to optimize performance. However, there is a limit to the amount of helium which can be used in a FAIMS analyzer. The maximum voltage which can be applied between the FAIMS analyzer plates is reduced, for example typically substantially reduced, when using gases other than pure nitrogen.

Another approach to increasing the ratio of $K_H/K_L$ is the use of chemical modifiers or carrier gas dopants to increase selectivity, resolution, and peak capacity in FAIMS. Dopants and gas modifiers are typically vapors, such as water, methanol, ethanol, propanol, or many other organic solvents. These dopants form complexes with ions during the low electric field portion of the waveform, reducing $K_L$. However, the presence of chemical modifiers can decrease performance for some analytes, either by chemical reactions which transfer charge from ions of interest to the chemical modifier, or through negatively impacting both $K_L$ and $K_H$ if ions do not desolvate during the high field portion.

In the methodologies described above, any improvement achieved in FAIMS performance for one compound or class of compounds by using a mixture of gases or modified carrier gas with chemical vapors is accompanied by a loss of performance for some other class of compounds. This loss in performance can reduce resolution, reduce peak capacity, or result in a loss of signal intensity. In addition, gas mixtures which contain a gas with a lower dielectric breakdown threshold, or include reactive gases, may shorten the operational lifetime of the instrument. Thus, the approaches previously taken in the art to optimize FAIMS performance have been met with limited success.

The presently disclosed subject matter provides methods and devices to optimize the carrier gas composition in a compound specific manner. By linking the composition or flow rate of a gas or gases making up the gas composition with the voltages being applied for FAIMS, analysis of a more specific separation can be performed. This improved analysis allows for improved resolution without severe ion discrimination or unacceptable losses in ion signal intensity. Multiple possible techniques for linking or coordinatingly controlling the scan of these two parameters is provided in the presently disclosed subject matter. By coordinating the control of the composition of the operating gas with the application of the operating voltages the presently disclosed subject matter provides FAIMS systems having a wide range of ion filtering characteristics such as high pass, low pass, or notch type filter profiles, which can be mass, charge, or compound type specific.

For example, most FAIMS analyzers use pure nitrogen as a carrier gas due to the convenience of combining FAIMS with electrospray ionization (ESI) sources which commonly use $N_2$ as nebulizer and drying gases. However, the addition of alternate gases into the $N_2$ flow can increase the resolution of FAIMS devices. Helium (He) is one of the lowest mass and least polarizable gases used in FAIMS separations and can increase the low field mobility. The use of He increases the resolution, but at the same time decreases sensitivity for low mass-to-charge ions because of increased transmission loss due to radial diffusion. However, a scan linking compensation voltage (CV) and percent He composition, as disclosed herein, can balance signal and resolution over a range of mass-to-charge values.

In some embodiments, at least two flow controllers, also referred to herein as flow or gas regulators, can be simultaneously controlled by an electronic controller which can control the scan of the compensation voltage applied to the FAIMS device. As the compensation voltage is scanned to higher values, the relative percentage of at least one non-reactive gas of a carrier gas mixture (such as nitrogen, helium, argon, krypton, or any other gases which do not cluster with, aggregate around, or chemically bind to ions during their time in the FAIMS analyzer) is decreased relative to the other gases in a mixture. This coordinated reduction in the concentration of one non-reactive gas coupled with scanned higher compensation voltages provides for the typically low resolution peaks associated with high mass to charge species, which elute at lower compensation voltages, to be sharper while the typically high resolution peaks, which in more traditional high percentage helium gas blends suffer high losses, are unaffected.

In some embodiments, at least two flow controllers or gas regulators can be simultaneously controlled by an electronic controller controlling the scan of the compensation voltage applied to the FAIMS device with a CV dependent gas concentration profile which is notched. This coordinated control of the gas composition and compensation voltage is such that over a range of voltages the gas composition changes at one or more pre-determined CV voltages to form a two state system. In some embodiments, this can eliminate peak overlap within a specific region of the spectrum without affecting transmission for other ions.

In some embodiments, a one flow controller is dedicated to the control of a desolvation gas, while a second controller is dedicated to the control of a carrier gas. This second controller can in some embodiments be scanned with an electronic controller controlling the FAIMS separation (either the asymmetric waveform or compensation voltage) to change the time of the separation due to changes in flow and mobility of the ion through the analyzer region. In some embodiments, this can be used to improve the resolution for ions which have short transit times under normal operating conditions, or to prevent sensitivity loss by using heavier gases to reduce diffusion perpendicular to the FAIMS electrodes for high mobility ions while allowing improved resolution for low mobility ions. Still yet, in some embodiments at least one flow controller is dedicated to controlling the carrier/desolvation gas while another controller is used to control the concentration of a reactive species in concert with the varying of voltages applied to the FAIMS device. By way of example and not limitation, a possible reactive species can be ammonia, chlorine, hydrochloric acid, oxygen, or any other gas which clusters with, aggregates around, or binds to an ion during the time the ion resides in the FAIMS analyzer. By scanning the flow of such reactive species only when desired the benefits can be realized without suffering performance loss. Further, by limiting introduction to relatively short periods, the instrument itself benefits from reduced contamination or corrosive effects from these reactive species.

Referring to FIG. 1, the block flow diagram depicts a methodology for optimizing carrier gas composition as a function of FAIMS analyzer voltage or scan time. In particular, FIG. 1 illustrates steps that can be employed in coordinating the control of gas composition and voltage when using a FAIMS analyzer to thereby improve resolution, sensitivity, and selectivity. In some embodiments, the ions are first generated and detected without separation, as depicted in the step generally designated 110. Once a stable signal is achieved, the electronics responsible for separation in FAIMS can be turned on and adjusted to the desired amplitude and waveform shape in a next step generally designated 120. With the electronics operating properly, a scan function or scan profile can be constructed where the gas composition is varied as a function of the compensation voltage, as depicted in the step generally designated 130. Alternatively, in some embodiments, the gas composition may be a function of dispersion voltage. Still yet, in some embodiments, the gas composition may be a function of both dispersion voltage and compensation voltage, e.g., the ratio of dispersion and compensation voltages.

With the scan function created, the analytical scan can be performed in a next step generally designated 140. Next, the spectrum can be evaluated, either by the user or a computer algorithm, by comparing the spectrum against user criteria as indicated in the step generally designated 150. If the separation is found to provide an adequate separation of species, while maintaining signal-to-noise ratios above a pre-determined threshold for peaks of interest, then the analysis is complete (step generally designated 160). If the separation is inadequate, as determined in the evaluation step 150, the scan function or scan profile of step 130 can be modified so as to improve the separation.

In some embodiments, methods are provided for operating a high field asymmetric ion mobility spectrometry (FAIMS) device and using a FAIMS device to separate ions in a sample, wherein the methods can comprise providing a FAIMS device having electrodes, supplying an operating gas to the FAIMS device, wherein a composition of the operating gas comprises a blend of at least two gases, applying a mixture of operating voltages to the electrodes to establish a separation field between the electrodes, applying a sample to be analyzed to the FAIMS device, coordinating the control of the composition of the operating gas with the application of the mixture of operating voltages, whereby a change in a voltage applied to the electrodes results in a change in the composition of the operating gas, and separating one or more ions in the sample.

Regarding the control of the composition of the operating gas, in some embodiments a change in the composition of the operating gas can comprise a change in the relative proportion of the at least two gases with respect to one another. In some aspects, the blend of at least two operating gases can comprise a blend of at least two non-reactive gases. Alternatively, in some aspects, the blend of at least two operating gases can comprise one or more reactive gas.

Regarding the control of the flow or pressure of the operating gas, in some embodiments the total flow or pressure of the operating gas within the FAIMS device can be held constant by increasing the flow or pressure of a first gas in the blend while simultaneously proportionally decreasing the flow or pressure of the remaining gas or gases. Alternatively, in some embodiments, the total flow or pressure of the operating gas within the FAIMS device is allowed to vary, either momentarily or continuously during the method of separating ions. In some embodiments, the flow or pressure of the operating gas can be separately controlled, and the at least two gases making up the composition of the operating gas can be combined at a single point either prior to, or at a connection with the FAIMS device. Still yet, in some aspects the flow or pressure of the operating gas can be separately controlled, and the at least two gases making up the composition of the operating gas can be introduced into the FAIMS device at separate points on the FAIMS device such that gases enter or leave the device through at least two distinct paths.

With regard to the coordinated control or linked scanning of the operating gas and operating voltages, in some aspects at least one operating voltage can be the compensation voltage, dispersion voltage, the combination of dispersion voltage and compensation voltage, or the ratio of dispersion and compensation voltages. In some embodiments, the coordinated control of the composition of the operating gas with the application of the mixture of operating voltages can be used to shift the position of a peak in a compensation voltage spectrum to improve ion selectivity or peak capacity. In some embodiments, the coordinated control of the composition of the operating gas with the application of the mixture of operating voltages can comprise scanning the operating gas composition while operating the FAIMS device, wherein a scan of the operating gas composition can be used as a way for signal intensity control.

In some aspects, the flow or pressure of one or more gases within the operating gas can be varied in a manner which results in the residence time of ions within the FAIMS device being voltage dependent. In some embodiments, the flow or pressure of one or more gases within the operating gas can be varied with voltage applied as a way of selectively modifying the diffusion rate of specific ions within the FAIMS device. In some embodiments, the flow or pressure of one or more gases within the operating gas can be varied in a manner which causes a change in the temperature of ions transmitted through the FAIMS device. In some embodiments, the flow or pressure of one or more gases within the operating gas or gaseous vapors can be varied to aid or inhibit the formation of ion-neutral complexes, clusters, products, or the formation of other species which result in changes to ion velocity within the FAIMS device.

In some embodiments, both the operating gas composition and voltages applied can be controlled to selectively transmit ions of a specific class or family. In some embodiments, the specific class or family belongs to the group of lipids, carbohydrates, peptides, proteins, hydrocarbons, or any other group of molecules sharing similar elemental composition and chemical properties. Likewise, in some embodiments, both the operating gas composition and voltages can be controlled to selectively transmit ions of differing chemical composition but similar physical characteristics. The physical characteristics can be, for example, mass, charge, ion cross-section, ion mobility, polarizability, hydrophobicity, boiling point, or electron affinity.

In some embodiments the presently disclosed subject matter provides a FAIMS device comprising a gas regulator in communication with a FAIMS analyzer, wherein the gas regulator provides for the introduction of an operating gas into the FAIMS analyzer, and a controller in communication with the gas regulator, wherein the controller is capable of varying the composition of the operating gas introduced into the FAIMS analyzer. In some embodiments, a gas regulator can provide for the introduction of an operating gas into a FAIMS analyzer at a single inlet on the FAIMS analyzer. In some embodiments, a FAIMS analyzer of the presently disclosed subject matter can comprise at least two gas regulators, wherein the at least two gas regulators provide for the introduction of at least two gases which comprise the composition of the operating gas. In some aspects, the at least two gas regulators can provide for the introduction of an operating gas into the FAIMS analyzer using at least two separate inlets on the FAIMS analyzer. Alternatively, in some aspects the two gas regulators can provide for the introduction of the operating gas into the FAIMS analyzer at the same inlet on the FAIMS analyzer. In some embodiments, the two gas regulators can provide for the introduction of a different gas comprising the operating gas introduced into the FAIMS analyzer.

In some embodiments, a FAIMS device of the presently disclosed subject matter can provide for the ability to varying the composition of the operating gas, which can comprise varying the flow or pressure of one or more gases being introduced into the FAIMS analyzer. In some aspects, the composition of the operating gas is varied as a function of a scanning voltage input from a FAIMS power supply to the FAIMS analyzer.

In some embodiments, a FAIMS device of the presently disclosed subject matter can comprise a gas regulator that is electronically controlled by a controller that is in electronic communication with the regulator. A controller can comprise a computer-readable medium having stored thereon instructions for controlling the regulator to thereby provide an operating gas composition as a function of a scanning voltage input from a FAIMS power supply.

Figure 2:
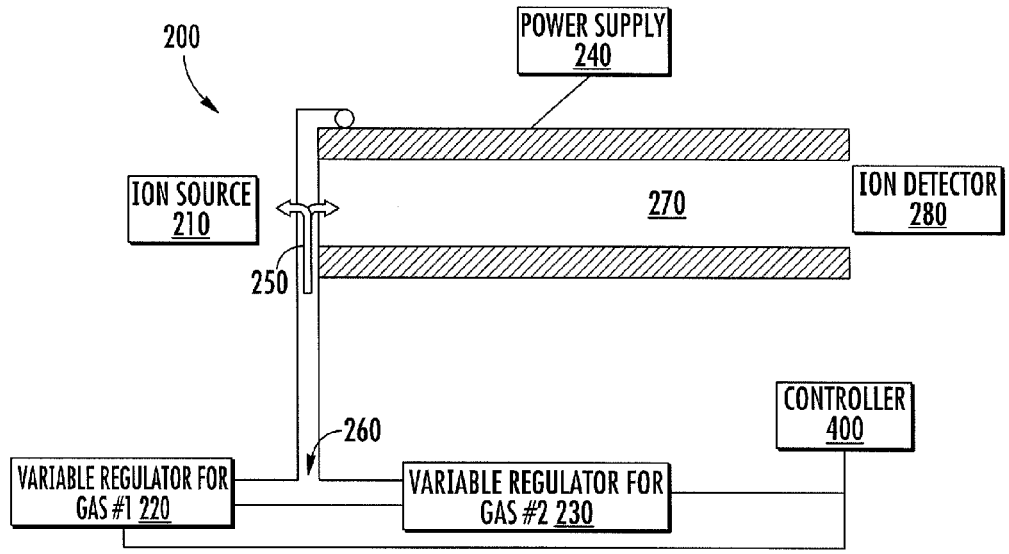
FIG. 2 is a schematic of a FAIMS analyzer which uses a combination of two separately regulated gases as both the counter current desolvation gas and the analyzer carrier gas.

A schematic of a FAIMS analyzer of the presently disclosed subject matter is provided in FIG. 2. In some embodiments, and as illustrated in FIG. 2, a FAIMS analyzer, generally designated 200, can use a combination of two separately regulated gases as both the counter current desolvation gas and the analyzer carrier gas. In some embodiments, FAIMS analyzer 200, as depicted in FIG. 2, can have the capability to utilize a linked scan of gas composition and voltage.

In some embodiments, a FAIMS analyzer 200 can comprise an ion source 210 from which species to be analyzed are generated, at least two variable gas flow or pressure regulators, generally depicted in FIG. 2 as 220 and 230, a controller 400 in communication with gas regulators 220 and 230, and a power supply 240. Power supply 240 can generate an asymmetric waveform and scanning compensation voltage necessary to separate ions based on the ratio of $K_H$ to $K_L$. In some embodiments, the gas output 250 from gas regulators 220 and 230 can be combined at a point 260 and mixed prior to acting as the carrier gas within FAIMS analyzer 200. Some percentage of the gas mixture maybe used as a desolvation gas while the remainder can act as the carrier gas to transport ions through the analyzer region, generally designated 270 in FIG. 2, towards an ion detector 280. Ion detector 280 may be an ion detector known in the prior art, including but not limited to a Faraday cup, channeltron, discrete dynode electron multiplier, or microchannel plate detector.

Figure 3:
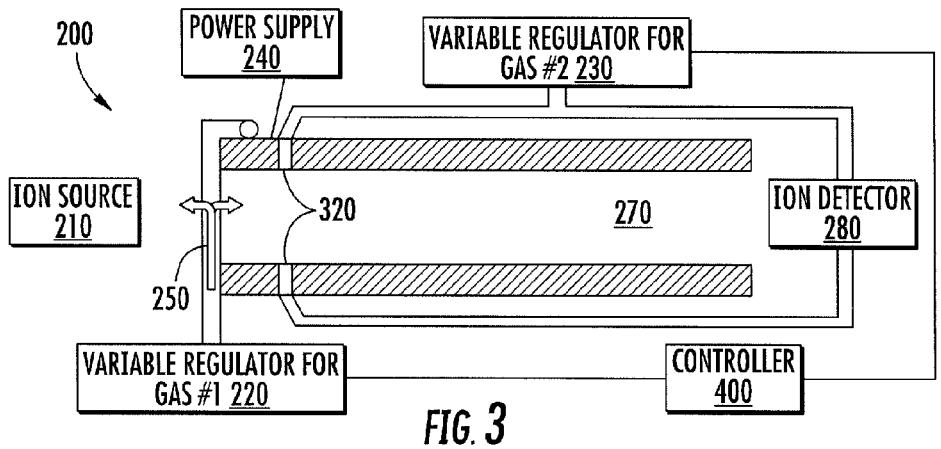
FIG. 3 is a schematic of a FAIMS analyzer which uses separate gas ports with the desolvation gas being split between desolvation and carrier gas, and a separate controller and ports for a dedicated carrier gas.

FIG. 3 is a schematic of a FAIMS analyzer using separate gas ports with the desolvation gas being split between desolvation and carrier gas, and a separate controller and ports for a dedicated carrier gas. In some embodiments, and as illustrated in FIG. 3, a FAIMS analyzer, generally designated 200, can use a combination of two separately regulated gases as both the counter current desolvation gas and the analyzer carrier gas. In some embodiments, a FAIMS analyzer 200 as illustrated in FIG. 3 can be largely similar to the FAIMS analyzer 200 illustrated in FIG. 2, with the exception of the point of entry of gases from gas regulators 220 and 230. That is, in some embodiments a FAIMS analyzer 200 of FIG. 3 can comprise an ion source 210 from which species to be analyzed are generated, at least two variable gas flow or pressure regulators 220 and 230, and a power supply 240. Power supply 240 can generate an asymmetric waveform and scanning compensation voltage necessary to separate ions based on the ratio of $K_H$ to $K_L$.

As depicted in FIG. 3, in some embodiments gas regulators 220 and 230 can provide a first and second gas, respectively, wherein the first and second gases are not combined at a point prior to entry into FAIMS analyzer 200 as in FIG. 2. Instead, in some embodiments a first gas output 250 regulated by gas regulator 220 can be partitioned between desolvation and carrier gas prior to entry into FAIMS analyzer 200 region 300 while a second gas regulated by gas regulator 230 enters FAIMS analyzer 200 at an inlet 320 or plurality of inlets 320 downstream in the analyzer region 270. In some embodiments, a second gas regulated by gas regulator 230 can be used only for the carrier gas and can allow for more exact control of gas composition within FAIMS analyzer region 270, particularly as compared to some embodiments such as that depicted in FIG. 2.

FIGS. 2 and 3 are schematics of FAIMS analyzers in planar geometries. The presently disclosed and claimed subject matter, including linking the composition or flow rate of a gas or gases making up the gas composition with the voltages being applied, can also be employed in FAIMS analyzers of cylindrical geometries.

Figure 4:
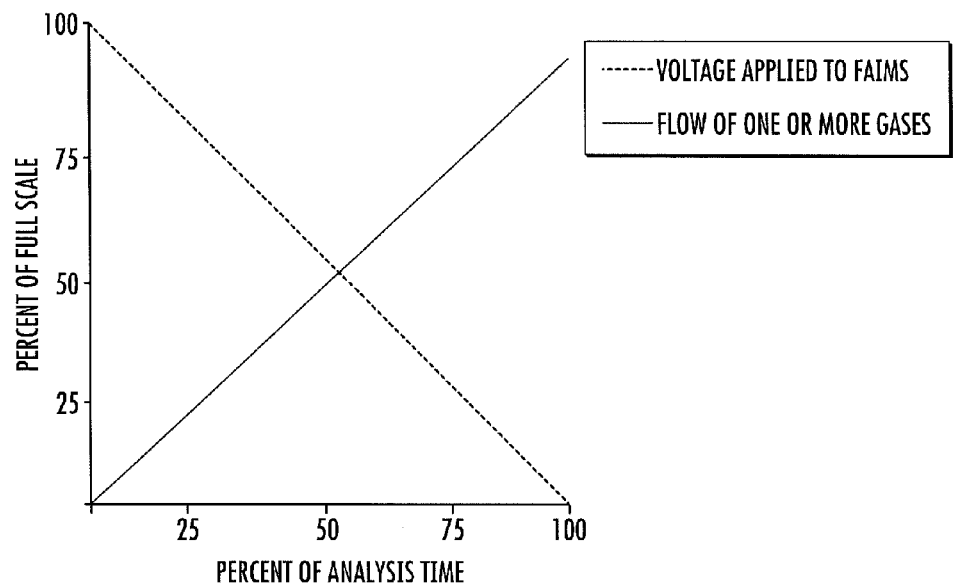
FIG. 4 is a graphical representation of a gas scan profile where the percent composition of at least one gas in a mixture decreases linearly with increasing voltage applied to the FAIMS analyzer.

In some embodiments, the carrier gas can comprise at least two component gases. FIG. 4 provides a graphical representation of the scan of a first component of the gas mixture as a function of the voltages applied to a FAIMS analyzer to perform ion separation. In this case a first gas in the blend is decreased linearly over the analysis while the voltage is increased linearly. A second gas which when combined with the first gas creates the mixture of gases used as the FAIMS carrier gas increases to maintain a constant flow or pressure through the system. In alternate embodiments, the flow rate or pressure of the carrier gas is allowed to vary with composition. In alternate embodiments, the concentration of the carrier gas, comprising any number of gases, may be varied according to any function of the FAIMS voltages.

Figure 5:
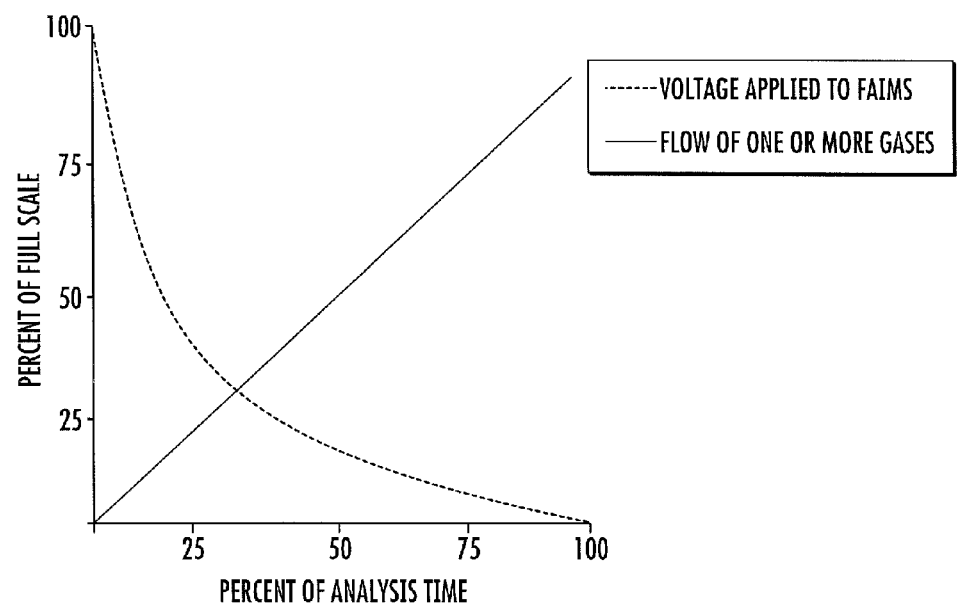
FIG. 5 is a graphical representation of a gas scan profile where the percent composition of at least one gas in a mixture decreases in a non-linear fashion with increasing voltage applied to the FAIMS analyzer.

In some embodiments, the concentration of a gas can change in a non-linear fashion with respect to the voltages applied during FAIMS analysis. For example, FIG. 5 depicts a graphical representation of a scan of a first component of a gas mixture as a function of the voltages applied to a FAIMS analyzer to perform ion separation. In this case the first gas in the blend is decreased in a non-linear fashion over the analysis while the voltage is increased linearly. A second gas, which when combined with the first gas creates the mixture of gases used as the FAIMS carrier gas, may increase to maintain a constant flow or pressure through the system. In alternate embodiments, the flow rate or pressure of the carrier gas is allowed to vary with the composition of the carrier gas. In alternate embodiments, the concentration in the carrier gas, comprising any number of gases, may be varied according to any function of the FAIMS voltages.

Figure 6:
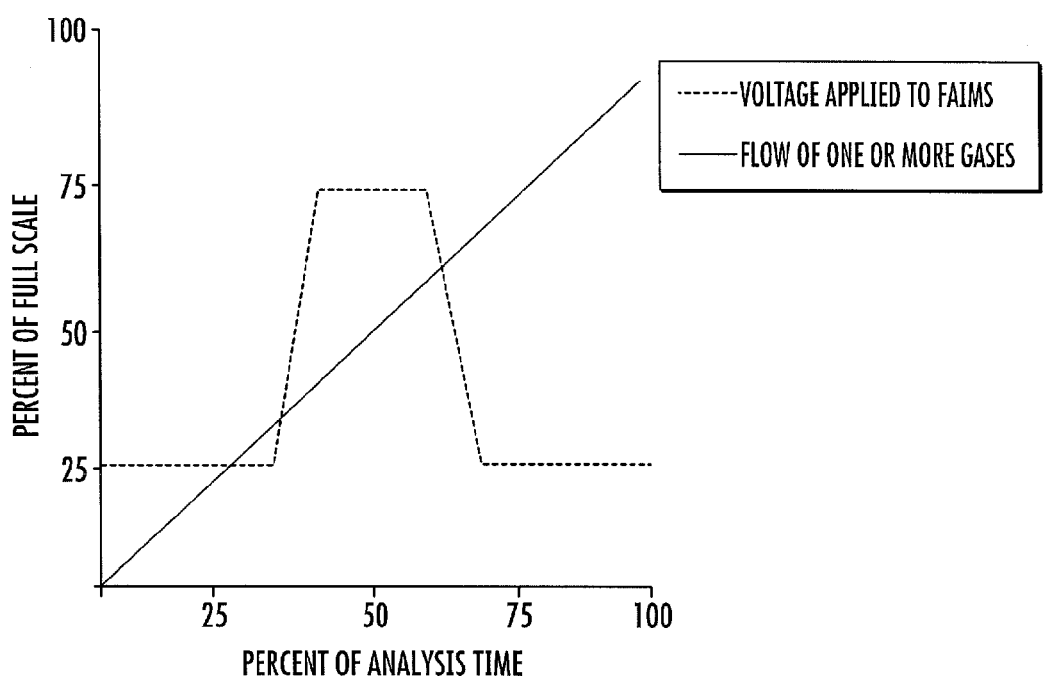
FIG. 6 is a graphical representation of a gas scan profile where the percent composition of a least one gas in a mixture forms a "notch" while scanning the voltage applied to the FAIMS analyzer.

In some embodiments, the concentration of a gas can increase and then decrease in a step-wise fashion with respect to the voltages applied during FAIMS analysis. For example, FIG. 6 depicts a graphical representation of the scan of a first component of a gas mixture comprising at least two gases with the voltages applied to a FAIMS analyzer to perform ion separation. In this embodiment, the first gas in the blend can be both increased and decreased over the analysis while the voltage is increasing linearly. In some embodiments, the first gas in the blend is increased and then decreased in a step-wise fashion. In one embodiment, the second gas, which when combined with the first gas creates the mixture of gases used as the FAIMS carrier gas, is varied to maintain a constant flow or pressure through the system. In alternate embodiments, the flow rate or pressure of the carrier gas is allowed to vary with composition. In alternate embodiments, the concentration in the carrier gas, comprising any number of gases, may be varied according to any function of the FAIMS voltages.

EXAMPLES

The following examples have been included to illustrate modes of the presently disclosed subject matter. In light of the present disclosure and the general level of skill in the art, those of skill will appreciate that the following examples are intended to be exemplary only and that numerous changes, modifications, and alterations can be employed without departing from the scope of the presently disclosed subject matter.

Materials and Methods Employed in Examples

Experiments described in the examples hereinbelow were performed on a Bruker Esquire 3000 mass spectrometer. The planar FAIMS device was constructed from 6 mm×25 mm electrodes spaced 0.3 mm apart. The device was designed to be coupled to a flared glass capillary ESI inlet, and mounts on an Apollo I source. Nitrogen gas was used as the nebulizing and counter-current drying gas, which also serves as the FAIMS carrier gas.

Samples of Angiotensin I, PEG 600 and Agilent electrospray calibrant solution (02421-60001) were used to determine the percent ion transmission and resolution with varying He concentrations. Helium was metered into the counter current gas line using an MKS model 1179 mass flow controller. The amount of helium was controlled by a LabVIEW program and ranged from 0% to 60%.

The total flow rate was 7 L/min for all experiments. For linked scans nitrogen and helium were both metered through MKS model 1179 flow controllers. The flow rate for linked scans was set to 2 L/min in the instrument software and the remaining flow was controlled through a Tenma power supply. An inverse linear relationship between the nitrogen and helium maintained the total output from the supply at 5 L/min. This flow combined to the 2 L/min flow from the instrument through a tee that entered prior to the heating block in the source.

Example 1

Figure 7:
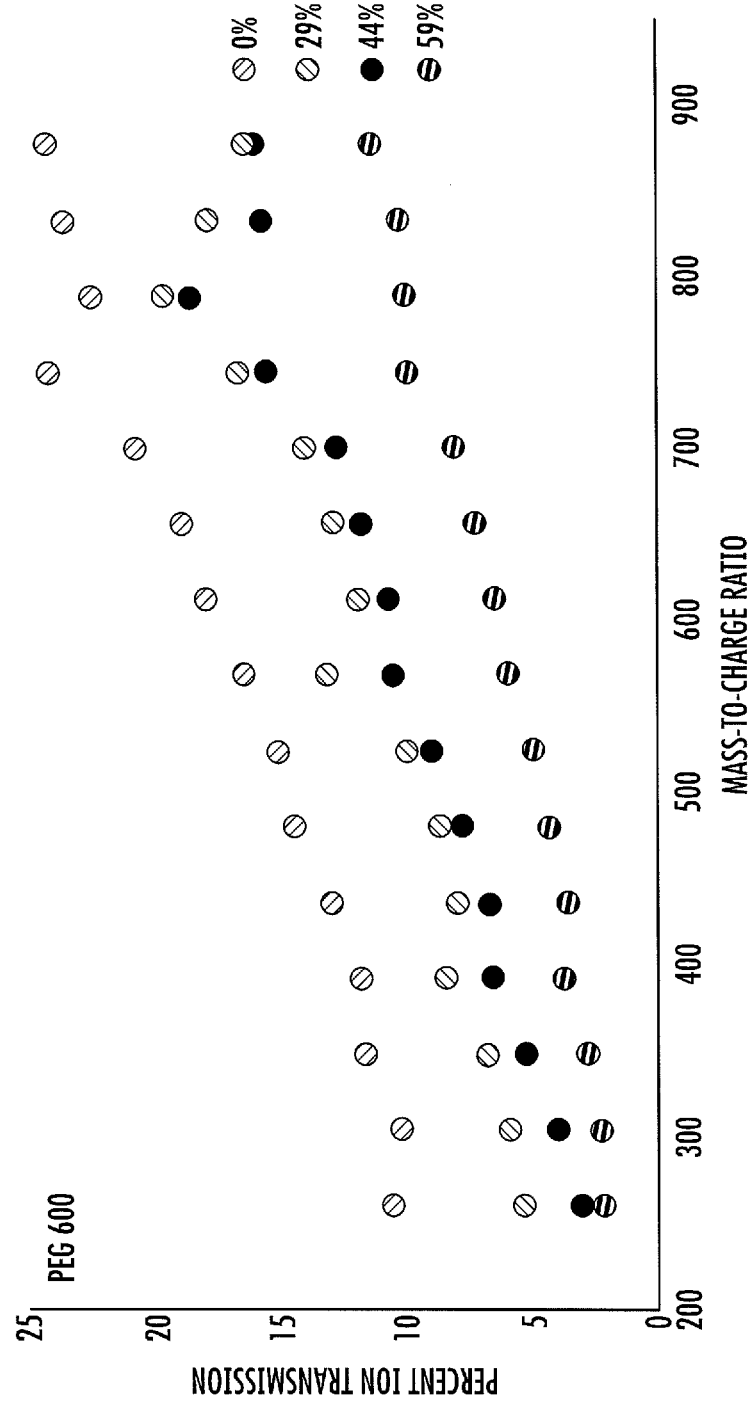
FIG. 7 is a graphical representation of the effects of helium (He) gas concentration in the carrier gas on ion transmission. All ions decreased in transmission with increasing percentage of He. Transmission decreased with a decrease in the mass-to-charge ratio.
Figure 8:
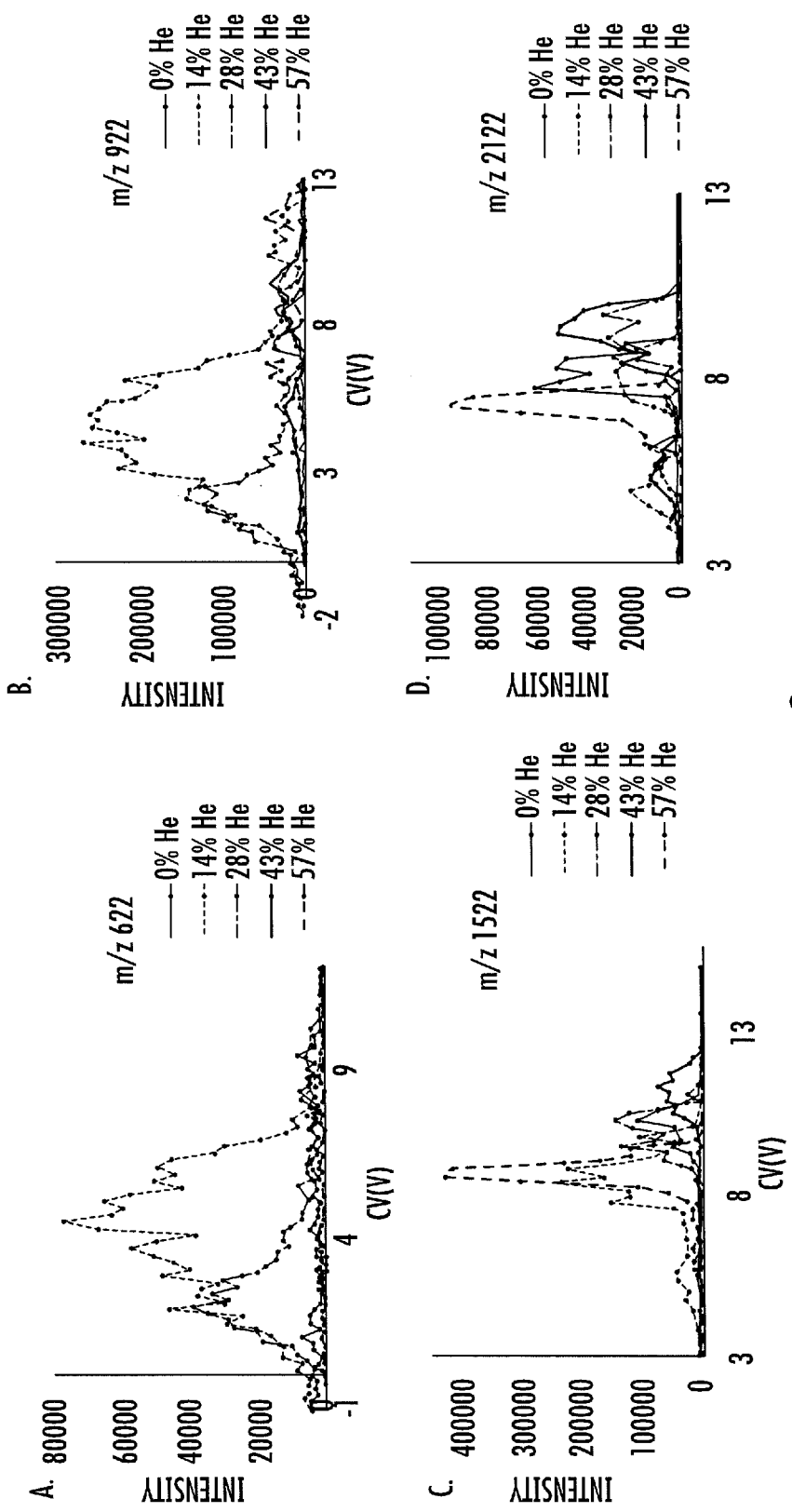
FIGS. 8A-8D are graphical representations depicting the effect of He concentration on ion resolution. Ions with mass-to-charge values of 622 (FIG. 8A), 922 (FIG. 8B), 1522 (FIG. 8C), and 2122 (FIG. 8D) were observed with percent helium compositions ranging from 0% He to 57%. Resolution increased with increasing percent He composition for higher m/z ions. Lower m/z ions were lost above 28% He.

PEG 600 was analyzed with the planar FAIMS grounded and the electrospray needle at 4.25 kV. $N_2$ flow was controlled through the Bruker software. Helium was added to produce carrier gas ratios ranging from 0% He to 60% He. Ratios above 60% He/40% $N_2$ were not possible due to pumping limitations of the instrument. The mass-to-charge values studied ranged from m/z 261 to m/z 789. All ions decreased in transmission with increasing percentage of He. See FIG. 7. At 60% He the lowest mass-to-charge ion, at m/z 261, decreased to 21% of its initial transmission when no He was added and the highest mass-to-charge ion at m/z 789 decreased to 43% of its initial transmission. The lower mass-to-charge ions' transmission was reduced relative to the higher mass-to-charge ions most likely due to increased diffusion rates in He.

Example 2

Figure 9:
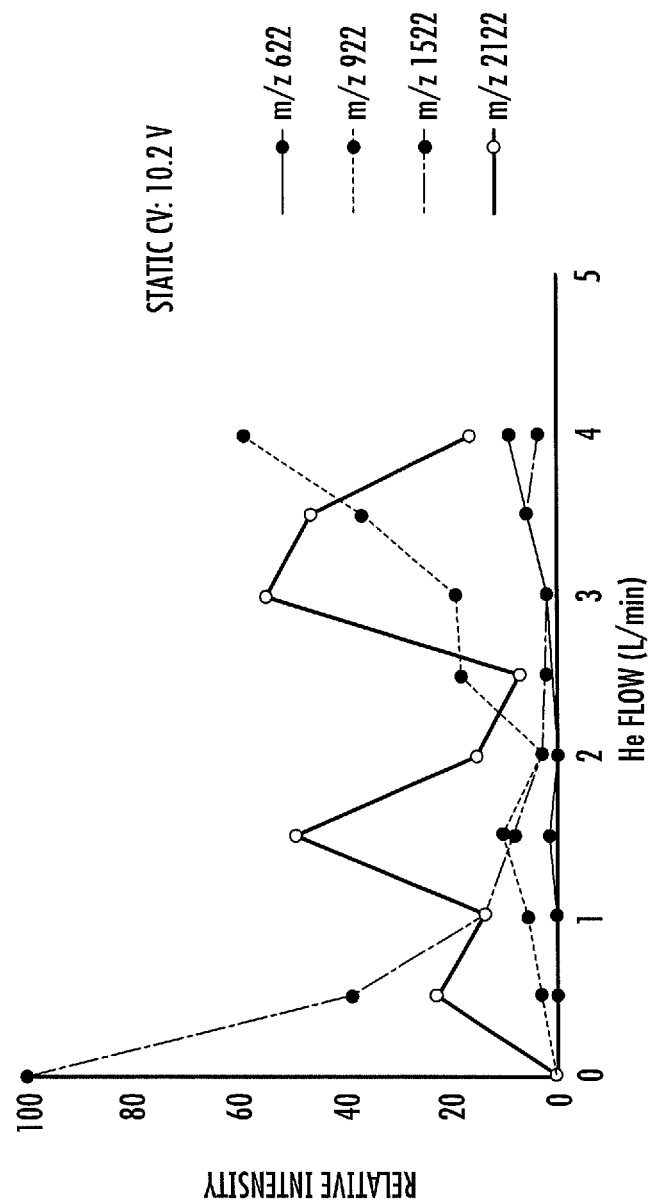
FIG. 9 is graphical representation illustrating the effect of scanning the percent He while the sample was held at a static CV on the ability to separate ions. Scanning across the percent He at a static CV allowed for the separation of a sample. Scanning the percent He composition also enabled the separation of two conformations of m/z 2122.

CV scans of Agilent electrospray calibrant solution with varying percentages of He were done to determine the effect on resolution. Ions with mass-to-charge values of 622, 922, 1522, and 2122 were observed with percent helium compositions ranging from 0% He to 57%. As shown in FIGS. 8A-8D, the resolution increased with increasing helium for m/z 1522, but smaller mass-to-charge ions were lost above 28% He. This sample was also held at a static CV and the percent He composition was scanned to successfully separate the sample. Scanning the percent He composition was also able to separate two conformations of m/z 2122. See FIG. 9.

Example 3

Figure 10:
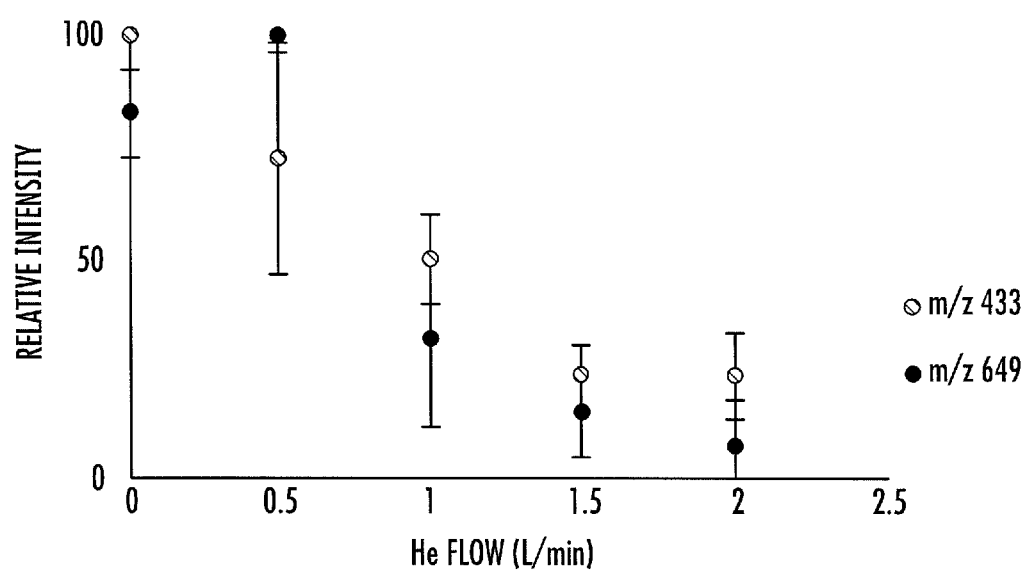
FIG. 10 is a graphical representation illustrating the effect of He concentration on the transmission of a smaller peptide. Results are shown for the peptide Angiotensin I. The intensities shown are relative to the maximum abundance for each of the charge states throughout the experiments. Percent transmission decreased for both charge states with the addition of 1 L/min He or more. A decrease in transmission limited separations with more than 1.5 L/min He.
Figure 11:
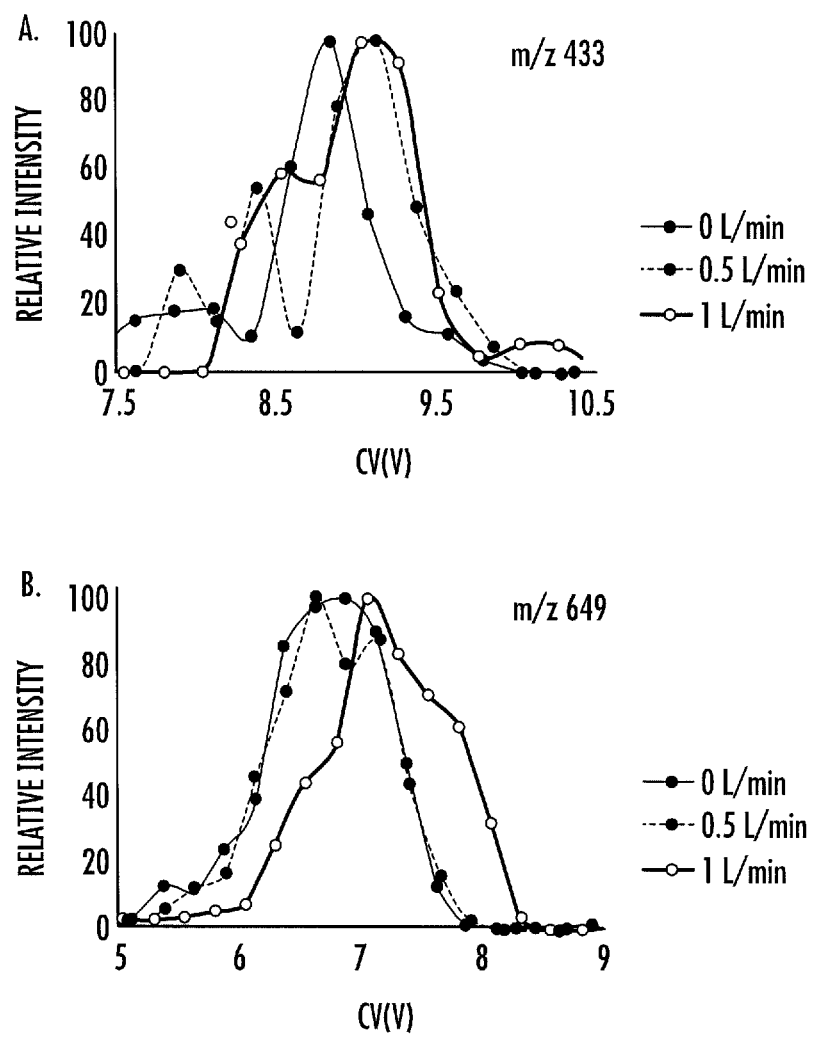
FIGS. 11A and 11B are graphical representations illustrating the effect of He concentration on the resolution of a smaller peptide. Results are shown for both charge states of the peptide Angiotensin I (m/z 433, FIG. 11A; m/z 649 FIG. 11B). The results show an increase in CV for both charge states of Angiotensin I. The resolving power for m/z 433 increased from 10.9 (0% He or 0 L/min) to 11.5 (14% He or 1 L/min).
Figure 12:
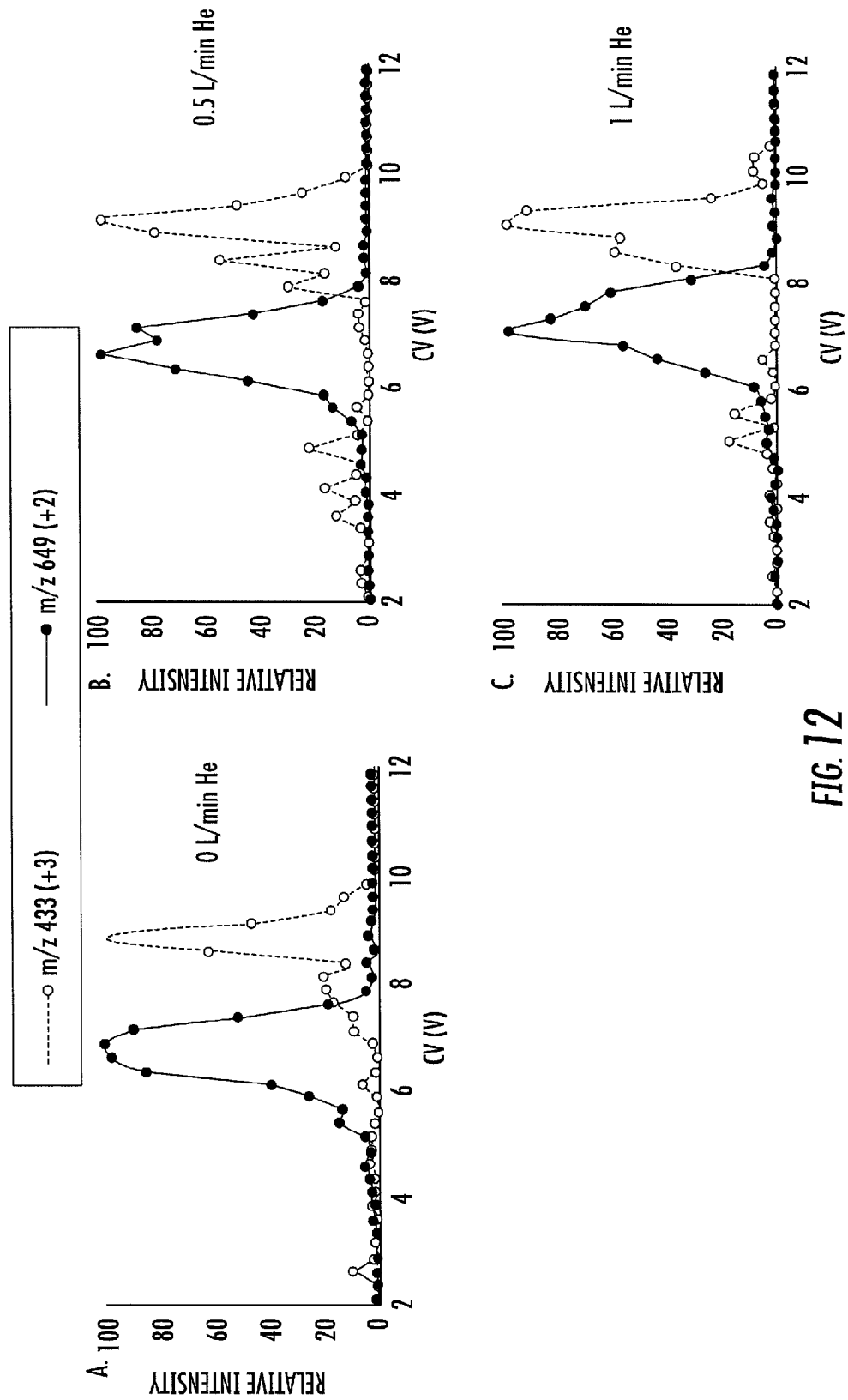
FIGS. 12A-12C are graphical representations illustrating the effect of He concentration on the separation of different charge states of Angiotensin I.

Angiotensin I was studied to determine the effect of He concentration on a smaller peptide. The percent transmission decreased for both charge states studied above 1 L/min He. See FIG. 10. This decrease in transmission limited separation capabilities for flow rates above 1.5 L/min He. See FIG. 10. The CV for both charge states increased with increasing percent He composition. The resolving power for m/z 433 increased minimally, from 10.9 (0% He) to 11.5 (14% He). See FIGS. 11A and 11B. Similar results for both m/z 433 and m/z 649 at 0 L/min He, 0.5 L/min He and 1 L/min He are shown in FIGS. 12A, 12B and 12C, respectively.

Example 4

Figure 13:
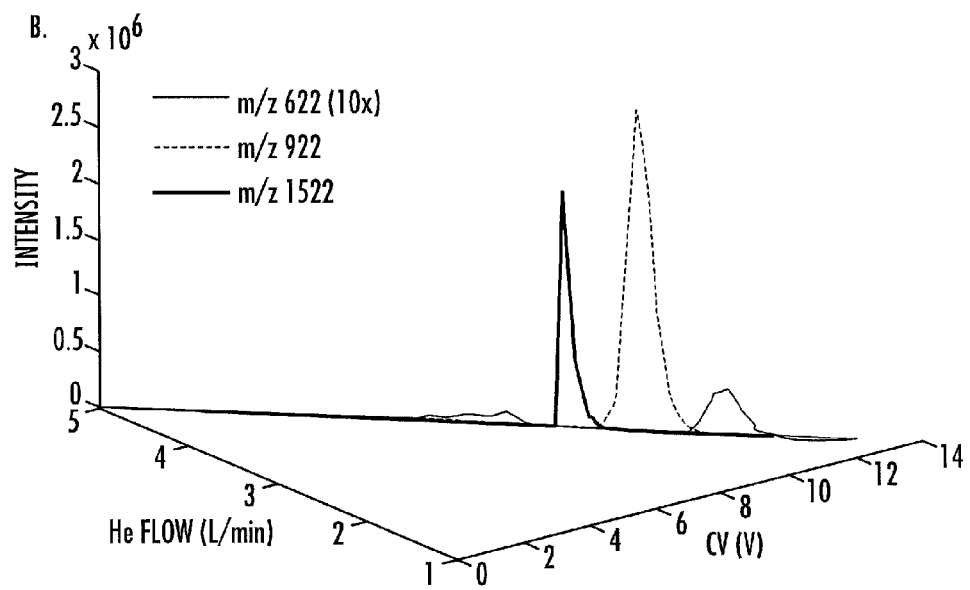
FIGS. 13A and 13B illustrate the effect of linked scanning on resolving power (RP), where percent He composition was scanned along with CV. Results are presented for ions with mass-to-charge values of 622, 922 and 1522.
Figure 14:
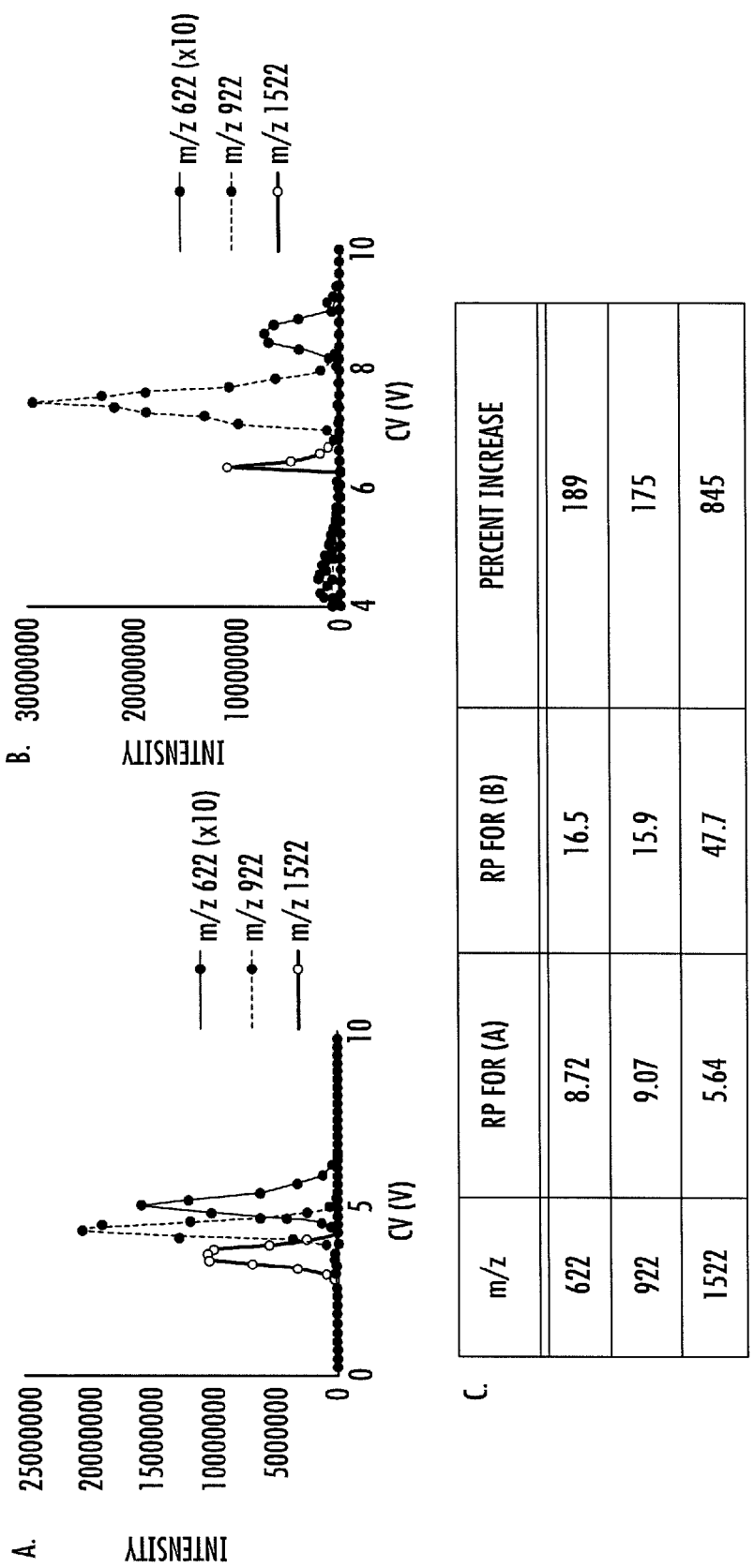
FIGS. 14A-14C illustrate the effect of linked scanning on resolving power (RP) or resolution.
Figure 15:
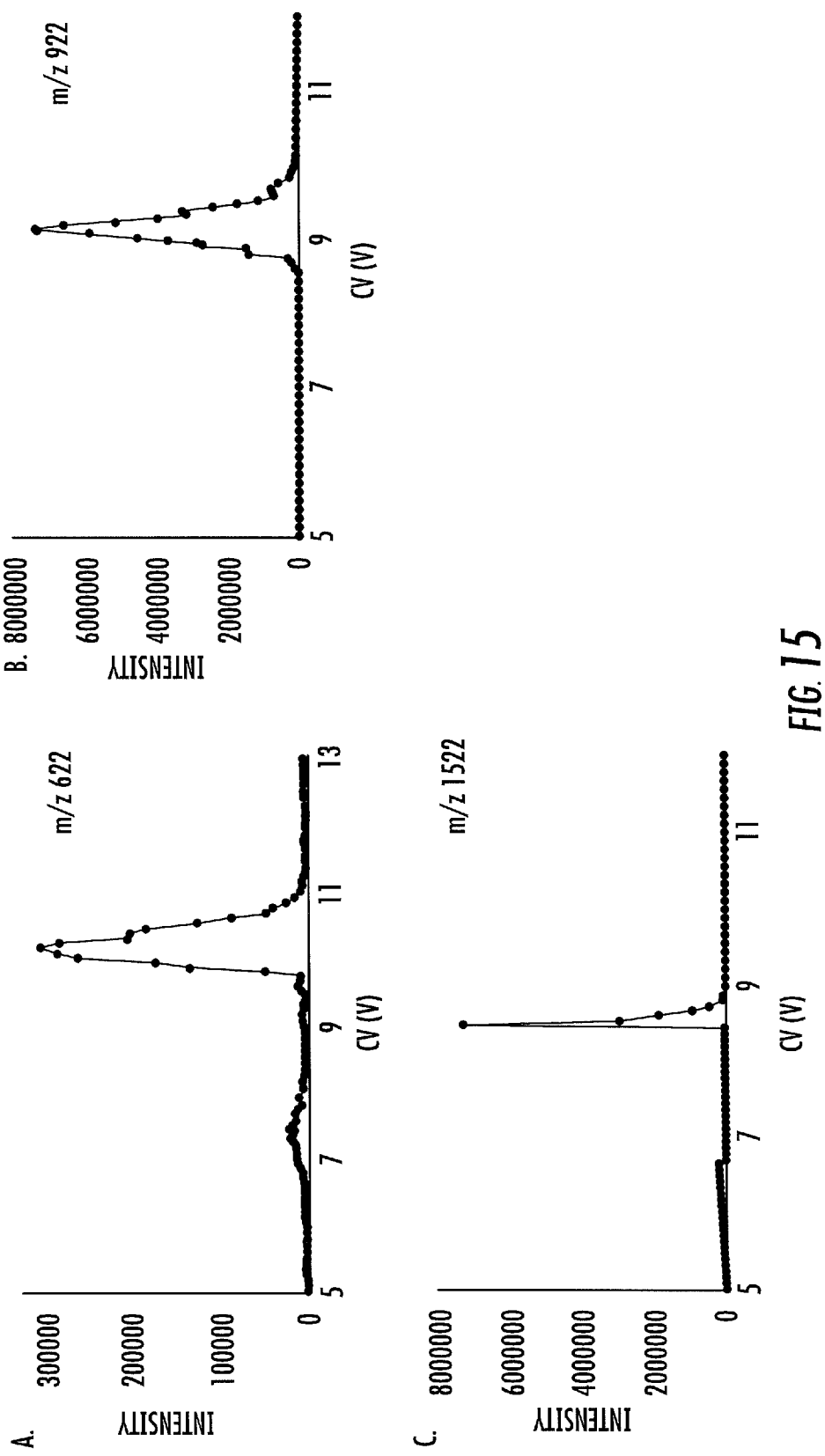
FIGS. 15A-15C are graphical representations illustrating the effect of linked scanning on RP of ions with mass-to-charge values of 622 (FIG. 15A), 922 (FIG. 15B) and 1522 (FIG. 15C). Using linked scanning the estimated resolving power is 18.0 for m/z 622, 25.1 for m/z 922 and 114 for m/z 1522. These results illustrate a large increase in RP compared to traditional CV scans.

Scans linking percent He composition with CV were done using the Agilent electrospray calibrant solution. The percent He composition was scanned from 57% to 0% while the CV was scanned from 5 V to 13 V. A linked scan for the calibrant solution is shown in FIG. 13. The average resolution for m/z 622 increased from 8.72 when no He was added to 16.9 with the linked scan. The average resolution for m/z 922 increased from 9.07 when no He was added to 19.6 with the linked scan. The average resolution for m/z 1522 increased from 5.64 when no He was added to 38.9 with the linked scan. The intensity of each ion decreased during the linked scan but transmission was still high enough to easily detect the ions. Data from similar experiments are provided in FIG. 14 where different slopes of the scan line (CV vs. He flow) have been used. In FIG. 15 a resolution of 114 was obtained for m/z 1522.

Example 5

Figure 16:
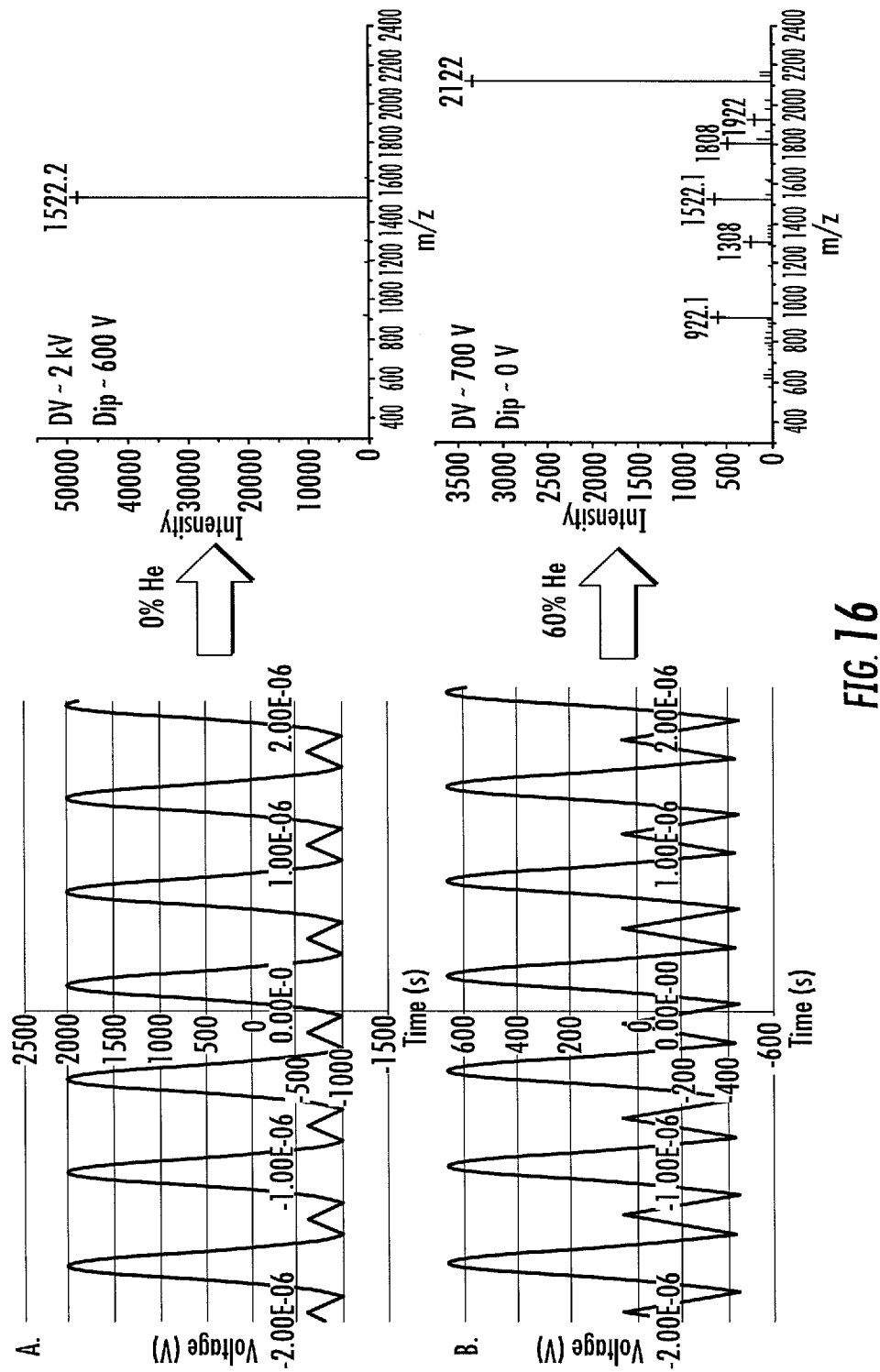
FIGS. 16A and 16B are graphical representations illustrating the effect of He on waveform.

FIGS. 16A and 16B are graphical representations illustrating the effect of He on dispersion voltage waveform. FIG. 16A illustrates the waveform when He concentration is 0%. FIG. 16B illustrates the waveform when He concentration is 60%. No changes were made to settings of the power supplies. The results illustrate that introduction of He to the system causes the waveform to change due to the change in the capacitance.

Example 6

Figure 17:
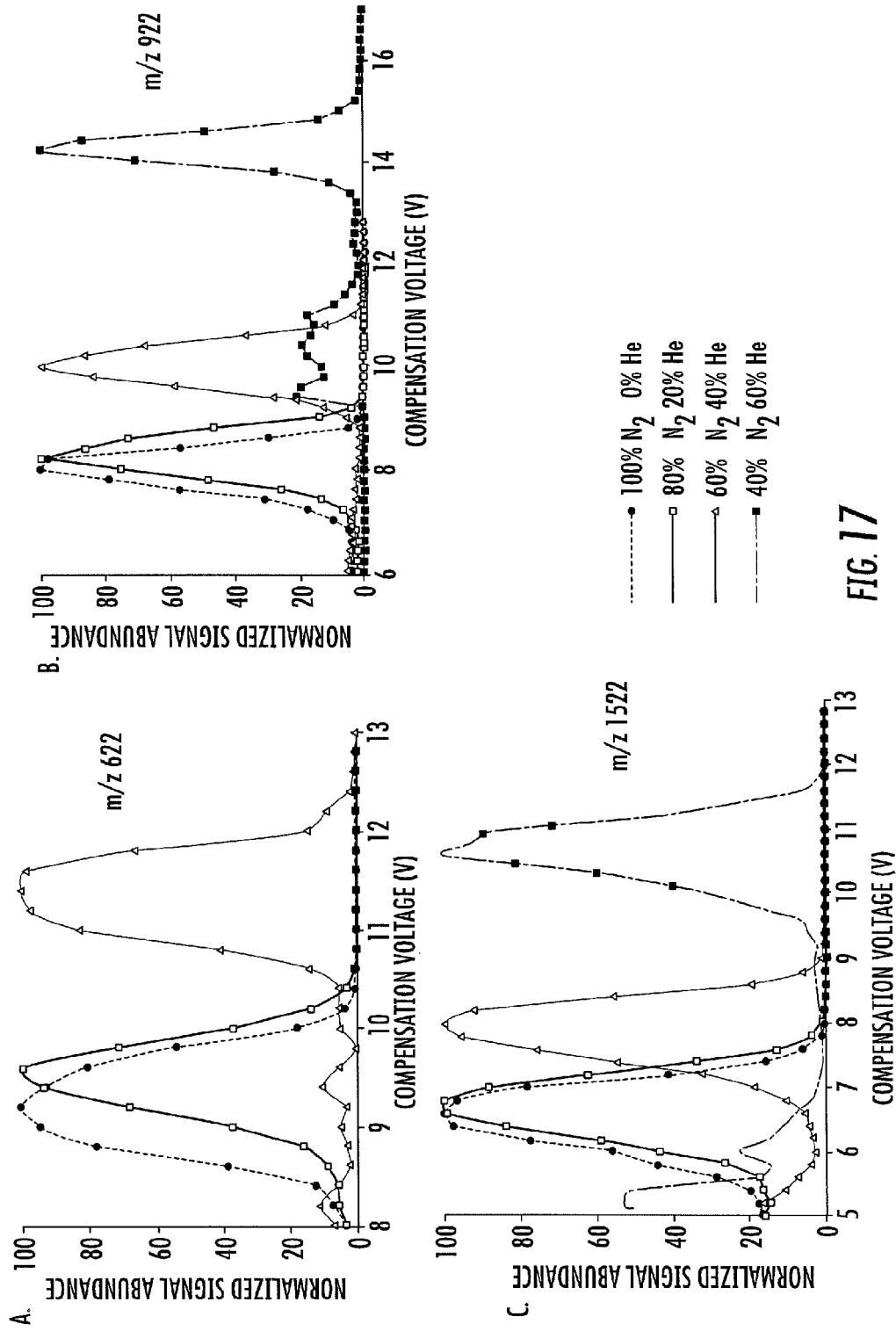
FIGS. 17A-17C are graphical representations illustrating the effect of changes in DV and Helium (He) on separation of ions with mass-to-charge values of 622 (FIG. 17A), 922 (FIG. 17B) and 1522 (FIG. 17C). For each ion (m/z 622, 922 and 1522), results are shown for gas compositions consisting of: 100% Nitrogen ($N_2$) and 0% He; 80% $N_2$ and 20% He; 60% $N_2$ and 40% He; and 40% $N_2$ and 60% He. Changes in DV and He improved separation.

FIGS. 17A-17C are graphical representations illustrating the effect of He on separation of ions with mass-to-charge values of 622 (FIG. 17A), 922 (FIG. 17B) and 1522 (FIG. 17C). For each ion (m/z 622, 922 and 1522) results are shown for gas compositions consisting of: 100% $N_2$ and 0% He; 80% $N_2$ and 20% He; 60% $N_2$ and 40% He; and 40% $N_2$ and 60% He. Increasing the percent He increases the mobility of the ion requiring an increase in the CV to transmit the ion to the mass spectrometer. The peak shape does not change significantly thus the resolving power increases.

Conclusions from Examples

The percent He composition was successfully scanned to separate a sample as well as two conformations of one of the ions within the sample. Changing the percent He composition also alters the FAIMS waveform which alters the separation. The presently disclosed and claimed subject matter provides methods and devices to scan CV and percent He composition simultaneously to thereby allow for the coordinated control of carrier gas composition and the voltages applied to a FAIMS analyzer. This scanning mode reduces the ion losses associated with using He while significantly increasing resolving power over traditional CV scans.

In some embodiments, resolving power is a characterization of how powerful a tool is for separating two very similar things. One way of doing this is to look at the characteristics of a single peak to determine how much phase space is available in the separation (i.e. how much time, voltage, or something else it takes to make the peak appear) and dividing that by how much space the peak takes up. Thus, in some aspects resolving power can be expressed as $$\frac{CV}{\Delta CV_{fwhm}},$$

or CV/full width have max CV of peak. For example, for a peak at a CV of 10V that is 1 V wide at the half maximum (or halfway down the peak), where all the peaks are of the same intensity and separation efficiency but for different components, and where for example 10 peaks are lined up and resolved down to the 50% line, the resolving power is 10.

It will be understood that various aspects or details of the presently disclosed subject matter may be changed, or various aspects or details of different embodiments may be arbitrarily combined if practicable, without departing from the scope of the presently disclosed subject matter. Furthermore, the foregoing description is for the purpose of illustration only, and not for the purpose of limiting the presently disclosed subject matter, which is defined solely by the appended claims.

What is claimed is:

1. A method of separating ions in a sample using a high field asymmetric ion mobility spectrometry (FAIMS) device, comprising:
   (a) providing a FAIMS device;
   (b) supplying an operating gas to the FAIMS device, wherein a composition of the operating gas comprises a blend of at least two gases;
   (c) applying a mixture of operating voltages to the FAIMS device to establish a separation field;
   (d) applying a sample to be analyzed to the FAIMS device;
   (e) coordinating control of the composition of the operating gas with the application of the mixture of operating voltages, whereby a change in a voltage applied to the FAIMS device results in a change in the composition of the operating gas, wherein the composition of the operating gas is scanned during the coordinated control of the composition of the operating gas and the application of the mixture of operating voltages;
   (f) separating one or more ions in the sample; and
   (g) simultaneously scanning the operating voltages and gas composition so as to filter components of the sample and successively transmit them through the FAIMS device, wherein the simultaneous scanning of the operating voltages and gas composition occur during the coordinated control of the composition of the operating gas and the application of the mixture of operating voltages.

2. The method of claim 1, wherein a change in the composition of the operating gas comprises a change in the relative proportion of the at least two gases with respect to one another.

3. The method of claim 1, wherein at least one operating voltage is the compensation voltage, dispersion voltage, the combination of dispersion voltage and compensation voltage, or the ratio of dispersion and compensation voltages.

4. The method of claim 1, wherein the blend of at least two operating gases comprises a blend of at least two non-reactive gases.

5. The method of claim 1, wherein the blend of at least two operating gases comprises one or more reactive gas.

6. The method of claim 1, wherein a total flow or pressure of the operating gas within the FAIMS device is held constant by increasing the flow or pressure of a first gas in the blend while simultaneously proportionally decreasing the flow or pressure of the remaining gas or gases.

7. The method of claim 1, wherein the total flow or pressure of the operating gas within the FAIMS device is allowed to vary, either momentarily or continuously during the method of separating ions.

8. The method of claim 1, wherein the flow or pressure of the operating gas is separately controlled, and the at least two gases making up the composition of the operating gas are combined at a single point either prior to, or at a connection with the FAIMS device.

9. The method of claim 1, wherein the flow or pressure of the operating gas is separately controlled, and the at least two gases making up the composition of the operating gas are introduced into the FAIMS device at separate points on the FAIMS device such that gases enter or leave the device through at least two distinct paths.

10. The method of claim 1, wherein the coordinated control of the composition of the operating gas with the application of the mixture of operating voltages is used to shift the position of a peak in a compensation voltage spectrum to improve ion selectivity or peak capacity.

11. The method of claim 1, wherein the coordinated control of the composition of the operating gas with the application of the mixture of operating voltages comprises scanning the operating gas composition while operating the FAIMS device, wherein a scan of the operating gas composition is used for signal intensity control.

12. The method of claim 1, wherein the flow or pressure of one or more gases within the operating gas is varied in a manner which results in the residence time of ions within the FAIMS device being voltage dependent.

13. The method of claim 1, wherein the flow or pressure of one or more gases within the operating gas is varied with voltage applied as a means of selectively modifying the diffusion rate of specific ions within the FAIMS device.

14. The method of claim 1, wherein the flow or pressure of one or more gases within the operating gas is varied in a manner which causes a change in the temperature of ions transmitted through the FAIMS device.

15. The method of claim 1, wherein the flow or pressure of one or more gases within the operating gas or gaseous vapors is varied to aid or inhibit the formation of ion-neutral complexes, clusters, products, or the formation of other species which result in changes to ion velocity within the FAIMS device.

16. The method of claim 1, wherein both operating gas composition and voltages applied controlled to selectively transmit ions of a specific class or family.

17. The method of claim 16, wherein the specific class or family belongs to the group of lipids, carbohydrates, peptides, proteins, hydrocarbons, or any other group of molecules sharing similar elemental composition and chemical properties.

18. The method of claim 1, wherein both operating gas composition and voltages are controlled to selectively transmit ions of differing chemical composition but similar physical characteristics.

19. The method of claim 18, where the physical characteristics are selected from the group consisting of mass, charge, ion cross-section, ion mobility, polarizability, hydrophobicity, boiling point, and electron affinity.

20. A method of operating a high field asymmetric ion mobility spectrometry (FAIMS) device, comprising:
(a) providing a FAIMS device;
(b) supplying an operating gas to the FAIMS device, wherein a composition of the operating gas comprises a blend of at least two operating gases;
(c) applying a mixture of operating voltages to the FAIMS device to thereby establish a separation field; and
(d) coordinating the control of the composition of the operating gas with the application of the mixture of operating voltages, whereby a change in a voltage applied to the FAIMS device results in a change in the composition of the operating gas, wherein the composition of the operating gas is scanned during the coordinated control of the composition of the operating gas and the application of the mixture of operating voltages; and
(e) simultaneously scanning the operating voltages and gas composition so as to filter components of the sample and successively transmit them through the FAIMS device, wherein the simultaneous scanning of the operating voltages and gas composition occur during the coordinated control of the composition of the operating gas and the application of the mixture of operating voltages.

21. The method of claim 20, wherein a change in the composition of the operating gas comprises a change in the relative proportion of the at least two gases with respect to one another.

22. The method of claim 20, wherein at least one operating voltage is the compensation voltage, dispersion voltage, the combination of dispersion voltage and compensation voltage, or the ratio of dispersion and compensation voltages.

23. The method of claim 20, wherein the blend of at least two operating gases comprises a blend of at least two non-reactive gases.

24. The method of claim 20, wherein the blend of at least two operating gases comprises one or more reactive gas.

25. The method of claim 20, wherein a total flow or pressure of the operating gas within the FAIMS device is held constant by increasing the flow or pressure of a first gas in the blend while simultaneously proportionally decreasing the flow or pressure of the remaining gas or gases.

26. The method of claim 20, wherein the flow or pressure of the operating gas is separately controlled, and the at least two gases making up the composition of the operating gas are combined at a single point either prior to, or at a connection with the FAIMS device.

27. The method of claim 20, wherein the flow or pressure of the operating gas is separately controlled, and the at least two gases making up the composition of the operating gas are introduced into the FAIMS device at separate points on the FAIMS device such that gases enter or leave the device through at least two distinct paths.

* * * * *